United States Patent [19]

Giesy et al.

[11] Patent Number: 5,152,749
[45] Date of Patent: Oct. 6, 1992

[54] INSTRUMENT PLACEMENT APPARATUS

[75] Inventors: Jerry D. Giesy; Matthew W. Hoskins, both of Portland, Oreg.

[73] Assignee: American Medical Systems, Inc., Minnetonka, Minn.

[21] Appl. No.: 722,886

[22] Filed: Jun. 28, 1991

[51] Int. Cl.⁵ ............................................. A61M 5/178
[52] U.S. Cl. .................................. 604/164; 604/272; 604/280
[58] Field of Search ................. 604/53, 166, 164, 165, 604/162, 280, 292, 239, 283, 285, 264

[56] References Cited

U.S. PATENT DOCUMENTS

| | | | |
|---|---|---|---|
| 4,431,426 | 2/1984 | Groshong et al. | 604/164 |
| 4,684,369 | 8/1987 | Wildemeersch | 604/272 |
| 4,762,519 | 8/1988 | Frimberger | 604/164 |
| 4,826,481 | 5/1989 | Sacks et al. | 604/164 |
| 4,869,717 | 9/1989 | Adair | 604/164 |
| 4,874,375 | 10/1989 | Ellison | 604/164 |
| 4,880,000 | 12/1989 | McQuilkin et al. | 604/164 |

OTHER PUBLICATIONS

Brochure by Northgate Research, Inc.

*Primary Examiner*—Gene Mancene
*Assistant Examiner*—Michael Lynch
*Attorney, Agent, or Firm*—Robert L. Harrington

[57] ABSTRACT

A surgical apparatus for the placement of an instrument within a body cavity which comprises (i) a placement device including an elongate element with an exposable tissue piercing tip, a first coupler adjacent to the tip, and a structure for selectively exposing the tip; and (ii) an elongate instrument for placement including a second coupler adapted to be coupled to the first coupler to effect an end to end coupling of the device and the instrument whereby the instrument is positioned within the body cavity. Preferably the instrument is a suprapubic instrument for placement within a bladder. A method for placement of a suprapubic instrument is also disclosed.

17 Claims, 3 Drawing Sheets

INSTRUMENT PLACEMENT APPARATUS

BACKGROUND OF THE INVENTION

The present invention relates to a surgical apparatus for the placement of an instrument within a body cavity. More particularly, the invention relates to an apparatus, device and method for suprapubic instrument placement.

Suprapubic catheters and instruments are used in many clinical settings including cases involving female incontinence, trans-urethral resection of the prostate where continuous irrigation is used, neurogenic bladders, spinal cord injury and other cases where bladder drainage and/or healing are desired. Additionally suprapubic instruments are used for inspection and therapy of the bladder, prostate, and/or ureter. Suprapubic catheterization offers a number of advantages over transurethral catheterization. These advantages include increased patient comfort, minimization of infection, improved irrigation and drainage during and after resection of the prostate, easier replacement and superior convenience during long-term catheterization, and improved evaluation of voiding and residual urine when applicable. Also, the suprapubic site is a convenient access route for instruments to observe and treat various conditions, the design, shape, and size of the instrument not being restricted by the shape and size of the urethra or concerns of urethral injury.

U.S Pat. No. 4,684,369 discloses a needle for introducing a suprapubic bladder drainage instrument through the urethra. The needle is adapted to be attached at its rear end to a catheter which follows the needle through the urethra.

Current methods of placing suprapubic catheters are the "outside-to-inside" method and the less common "inside-to-outside" method. With the outside-to-inside approach, a sharp trocar or catheter-obturator combination is used to pierce from outside the body through the lower abdomen and into the bladder to create a passageway for pushing the catheter into the bladder. By comparison, the inside-to-outside method employs a grasping tool which is passed into the bladder via the urethra and, after positioning, can be pressed through the bladder and abdominal wall near the symphysis. Then grasping the catheter, it is used to pull the catheter into the bladder where the catheter may be released and left in a suprapubic placement.

While complications are rare, difficulties have been reported with percutaneous outside-to-inside suprapubic catheterization using a trocar. For example, the catheter may be placed accidentally outside of the bladder. The standard method of using a trocar/catheter arrangement does not always provide the accuracy and control needed for correct placement of the catheter. Also, outside-to-inside catheterization presents risk of injury to the floor of the bladder or damage to the bowel. Uncertainties in trocar alignment, orientation, or insertion distance can lead to such injuries. Thus, poor alignment or variable depth can result in perforation of the peritoneum, incomplete bladder entry, or penetration of the posterior bladder wall. Furthermore, due to a limited choice of catheter sizes and types, inadequate catheter lumen size may result. Finally, inappropriate suprapubic puncture size may result in extravasation of urine around the catheter or into the retroperitoneum.

Use of the inside-to-outside technique can minimize the above problems, but the lack of well designed devices for performing the procedure has limited its adoption. With the inside-to-outside method, a curved grasping tool is passed through the urethra and its tip is pushed against the bladder dome and anterior abdominal wall. Suprapubic palpation enables the practitioner to select a desired penetration site. The curved tool is pressed against the bladder dome and in some cases forced through the bladder, fascia, and abdominal wall. In other techniques, an incision is extended from the exterior abdominal wall on to the instrument tip permitting its advancement. Once outside the abdomen, the device is coupled to the drainage tube in some fashion so that the tube is guided into the bladder. Once within the bladder, the drainage tube is released. The device is then removed by way of the urethra.

While various instruments which utilize the inside-to-outside approach exist, none have coordinated the penetration, coupling, and release functions. Currently used instruments include the Lowsley retractor, uterine packing forceps (for females), and modified urethral sound. In general, these instruments require many steps, lack uniformity, and are not always readily available. Use of such instruments often results in ineffective penetration, inadvertent loss of the catheter, and poor sealing between the catheter and bladder wall.

The present invention provides improvement in the art of inside-to-outside suprapubic instrument placement.

Improvements in the suprapubic instrument placement may be applied to other medical applications. For example, in substantially non-invasive methods of internal operations, e.g. laproscopic surgery, the practitioner accesses internal organs through small incisions and working sheaths. The instruments used in such operations are generally elongate and adapted for use by way of these small incisions or sheaths. Accordingly, improvements in placement of suprapubic instruments, which are generally elongate instruments, may be applied to such substantially non-invasive operations.

SUMMARY OF THE INVENTION

In accordance with a preferred embodiment of the present invention there is provided a surgical apparatus for the placement of an instrument within a body cavity which comprises (i) a placement device including an elongate element with an exposable tissue piercing tip, a first coupling means adjacent to said tip, and means for selectively exposing said tip; and (ii) an elongate instrument for placement including a second coupling means adapted to be coupled to said first coupling means when said tip has been exposed and operated to pierce a desired tissue site associated with said body cavity and establish a passageway through said tissue. The first and second coupling means are adapted to be mutually engaged to effect an end to end coupling of said device and said instrument whereby said instrument is positioned within said body cavity.

In the preferred embodiment of the apparatus the first coupling means and second coupling means are adapted to engage and disengage said device and said instrument in end to end relationship by relative lateral movement therebetween. It is also preferred that one of said first coupling means and said second coupling means includes locking means for securing said end to end coupling of said device and said instrument against decoupling by relative lateral movement therebetween.

A particular preferred embodiment is one in which the elongate element is a needle and the tissue piercing tip is the tip of said needle, said first coupling means is positioned adjacent the needle tip, and said locking means comprises a sheath slidable on said needle, whereby said sheath may be advanced over said needle tip and said first coupling means to selectively shield said tip and to lockingly envelop said second coupling means upon said first coupling means.

The invention also provides a placement device for the placement of an instrument within a body cavity, which instrument has a proximal end with instrument coupling means attached thereto, which device in a particular embodiment comprises:

a needle having a proximal end and a distal end with a tip adapted to pierce body tissue;

a sheath adapted to slidably accommodate said needle, one of said needle and said sheath being substantially rigid and the other of said needle and said sheath being flexible and adapted to conform in shape with the substantially rigid needle or sheath, one of said needle and said sheath having device coupling means adapted to couple with said instrument coupling means; and handle means located at the proximal end of said needle and operatively coupled to said needle and said sheath to enable the needle and sheath to be moved relative to each other to selectively expose the tip of the needle beyond said sheath.

Preferably the device coupling means is an indentation adapted to couple with an instrument coupling means in the form of a loop. In a particularly preferred embodiment the indentation is adjacent said needle tip and the engagement of the loop with the indentation is adapted to be lockingly enveloped with the sheath when said sheath is advanced over said needle tip. It is also preferred that the needle is substantially rigid and the sheath is flexible.

In an alternative embodiment the instrument coupling means is a ball and stem attached to the proximal end of the instrument and the device coupling means comprises a cavity and groove adapted to accommodate said ball and stem and the engagement of the two coupling means is adapted to be lockingly enveloped within the sheath when the sheath is advanced over the needle tip.

Preferably the instrument to be placed by the device is adapted for suprapubic placement and said substantially rigid one of said needle and said sheath is adapted in shape for insertion within a selected urethra.

When the selected urethra is a female urethra said shape comprises a proximal straight length portion and a distal straight length portion connected by a curved length portion establishing an angular relationship between said proximal and distal portions. Alternatively, when the selected urethra is a male urethra said shape comprises a proximal straight length portion, a first curved length portion and a central straight length portion, establishing an angular relationship between said proximal and central portions; a second curved length portion and a distal straight length portion, establishing an angular relationship between said central portion and said distal portion.

The invention further provides a coupling mechanism for coupling an elongate instrument to a placement device whereby said instrument may be placed within a body cavity, which coupling mechanism in a preferred embodiment comprises;

instrument coupling means attached to a proximal end of said elongate instrument and device coupling means adjacent a distal end of said placement device wherein said instrument coupling means is adapted to operatively engage with or disengage from said device coupling means by relative lateral movement between said instrument sand said device to thereby couple said instrument to said device so that the coupling is secure against relative longitudinal movement between said instrument and said device; and locking means for selectively resisting said lateral movement between said instrument and said device and thereby lock said coupling mechanism.

In the preferred embodiment of the coupling mechanism the coupling means may comprise:

an indentation on one of said instrument and said device; and a loop on the other of said instrument and said device, the loop being adapted to be positioned and retained within said indentation by relative lateral movement between said instrument and said device.

In an alternative embodiment of the coupling mechanism the coupling means comprise:

a groove and cavity on one of said instrument and said device; and a stem and ball on the other of said instrument and said device, said ball being adapted to be accommodated within said cavity by relative lateral movement between said instrument and said device.

Preferably the locking means of the coupling mechanism comprises a sheath slidably disposed upon one of said instrument and said device and adapted to be slidably moved to envelop said coupling mechanism to resist relative lateral movement between said instrument and said device when said coupling mechanism couples together said instrument and said device.

The invention still further provides a method for the placement of a suprapubic instrument within the bladder of a patient, which in a preferred embodiment comprises;

inserting within said patient's urethra a sheathed needle having a distal end with a tissue piercing tip, said needle conforming in shape to the urethra, urging said sheathed needle tip against said patient's bladder dome to identify by palpation a penetration site, exposing said needle tip from within the sheath and piercing the bladder wall and abdominal wall to deliver tip exterior of the body, coupling to the distal end of said needle an instrument to be suprapubicly placed and advancing the sheath over the coupling to avoid disengagement of the coupling, drawing said instrument through the abdominal wall and into the bladder by partial retraction of said sheathed needle from the urethral sound, positioning said instrument as desired within the bladder, decoupling said needle from said instrument, and withdrawing aid sheathed needle from the urethral sound.

BRIEF DESCRIPTION OF THE DRAWINGS

The invention will be more particularly described with reference to preferred embodiments as illustrated in the accompanying drawings, in which.

DETAILED DESCRIPTION OF THE INVENTION

Instrument placement in accordance with a preferred embodiment of the present invention as applied to suprapubic instrument placement uses a placement device comprising a needle similar in shape to that of the urethral sound, slidably disposed within a sheath sized to suitably dilate the puncture made by the needle. The distal tip of the needle coupling means adjacent thereto configured such that it accepts and couples with a mating coupling means attached to the instrument, e.g., catheter to be pulled into the bladder. The preferred structure of the coupling means on the needle and the instrument to be pulled into the bladder is such that the instruments cannot be pulled apart in the direction of their longitudinal axis, yet may be disengaged in response to lateral forces. To more fully secure the needle and instrument while drawing the instrument into the bladder, the sheath is advanced over the tip of the needle to prevent the instrument coupling means from releasing from the needle tip coupling means.

Figures 1, 2:
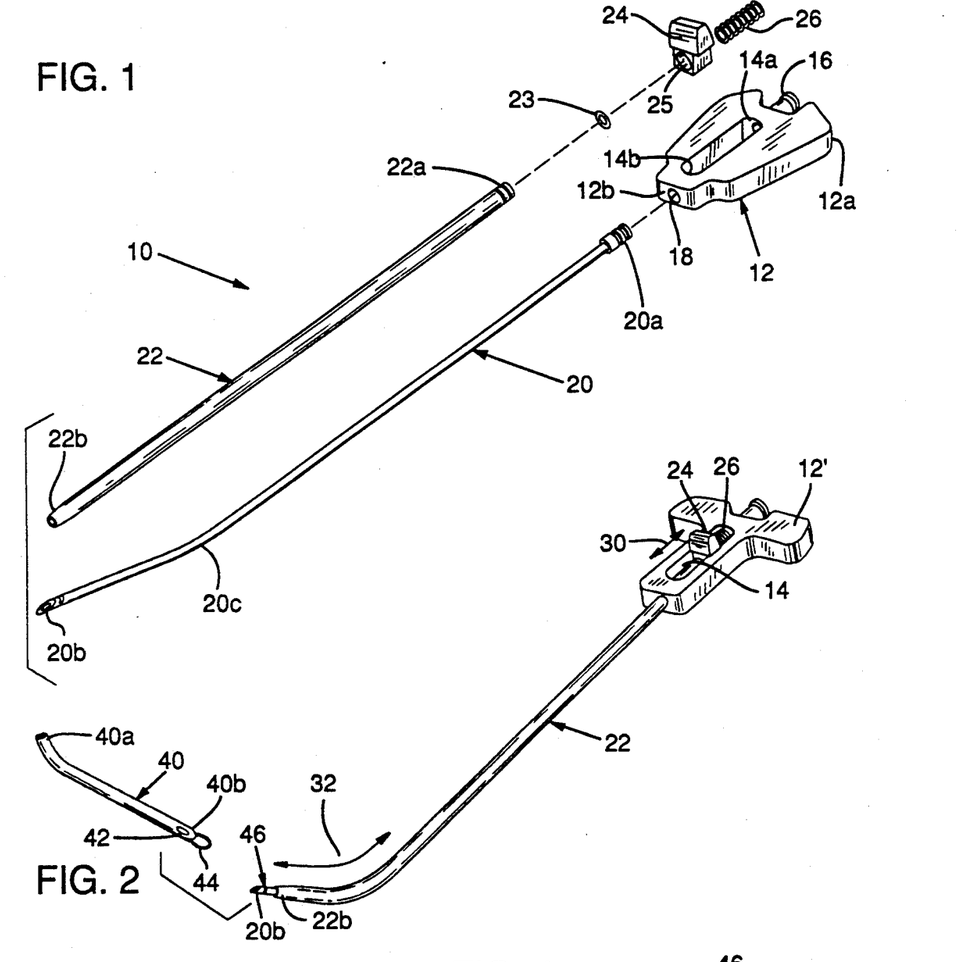
FIG. 1 is an exploded perspective view of a suprapubic instrument placement device in accordance with the present invention.
FIG. 2 illustrates a suprapubic instrument placement device similar to that of FIG. 1, but with an alternative handle shape and assembled to illustrate its coupling relationship to a catheter having a mating coupling means thereon.

The preferred embodiment illustrated in FIG. 1 of the drawings comprises a suprapubic instrument placement device 10 which includes a handle 12 with a central slot 14 therein. A luer lock hub 16 is mounted upon handle 12 between the proximal end 12a of the handle and the proximal end 14a of the slot. At the distal end 14b of the slot, an aperture 18 coaxial to hub 16 passes from the distal end 12b of the handle to the distal end 14b of the slot. A rigid needle 20 is accommodated within aperture 18 and couples at its proximal end 20a to the hub 16 at the proximal end 14a of slot 14. In the illustrated embodiment needle 20 is substantially straight but includes a bend 20c to provide a distal end portion which makes an angle of approximately 15 degrees with the main portion of the needle whereby needle 20 conforms generally in shape to that of a urethral sound.

A flexible sheath 22 slidably mounts upon needle 20 and conforms to the shape of needle 20. A proximal end 22a of sheath 22 threadably connects to a thumb piece 24 at a threaded aperture 25 thereof. An O ring 23 is interposed between the proximal end 22a of sheath 22 and thumb piece 24 for sealably coupling sheath 22, thumb piece 24, and needle 20. Thumb piece 24 is slidably positionable within the slot 14 with a smaller diameter portion of aperture 25 (not shown) closely receiving needle 20 for slidable mounting thereon. The aperture 25 of thumb piece 24 is desirably of two diameters, a larger diameter threaded portion closest to distal slot end 14b adapted to receive the proximal end 22a of sheath 22 and the above-mentioned lesser diameter portion closest to proximal slot end 14a adapted for slidably receiving the needle 20. A spring 26 mounts coaxially upon the needle 20 near its proximal end 20a and is located between the thumb piece 24 and proximal slot end 14a to bias thumb piece 24 toward the distal slot end 14b.

The needle 20 is rigidly affixed to the handle 12 at hub 16. Thumb piece 24 is slidably positioned upon the portion of the needle 20 residing within slot 14. Also, spring 26 biases thumb piece 24 toward the distal end 14b of slot 14. The O ring 23 slides down the length of needle 20 and into slot 14 for positioning within the aperture 25 of thumb piece 24. Sheath 22 is then positioned upon needle 20 by inserting the distal end 20b of needle 20 through the proximal end 22a of sheath 22 whereby the proximal end 22a of sheath 22 may be threadably mounted within the aperture 25 of thumb piece 24. Accordingly, sheath 22 may be selectively mounted and dismounted from the device 10. It is contemplated that several such sheaths 22 may be provided of various diameters whereby a suitable sheath diameter may be selected corresponding to the diameter of the instrument to be suprapubicly placed. In this manner, sheath 22 performs a dilating function to closely match the diameter of the passageway provided between the bladder and the abdominal wall with the diameter of the instrument to be suprapubicly placed.

The proper relative length of needle 20 and sheath 22 as compared to the length of slot 14, i.e., range and movement for thumb piece 24, enables the user of device 10 to selectively expose the distal end 20b of needle 20 beyond the distal end 22b of sheath 22 by operation of thumb piece 24 within slot 14.

FIG. 2 illustrates a suprapubic instrument placement device 10 in its assembled configuration, but having a T shaped handle 12'. In other respects, the devices 10 of FIGS. 1 and 2 can be identical. The shape of handle 12 and handle 12' provides the practitioner with a reference for orientation of the distal end 20b of needle 20. A practitioner familiar with the shape and orientation of handle 12 relative to the orientation of needle 20 more accurately positions the distal end 20b of needle 20 during suprapubic instrument placement. In operation, needle 20 remains fixed relative to handle 12', but sheath 22 moves relative to handle 12' by movement of thumb piece 24 within slot 14. More particularly, movement of thumb piece 24 as indicated by arrows 30 corresponds to movement of the distal end 22b of sheath 22 relative to the distal end 20b of needle 20 as indicated by arrows 32. In this manner, the distal end 20b of needle 20 may be selectively exposed at the distal end 22b of sheath 22.

FIG. 2 also illustrates a catheter 40 including an inlet opening 42 for passage of fluids through catheter 40 to the proximal end 40a of catheter 40. The distal end 40b of catheter 40 includes a loop 44 comprising a length of filament material forming a closed loop and passing through a solid portion of the tip, i.e. the end 40b, of catheter 40. Loop 44 thereby provides a secure structure for attachment to an indentation or notch 46 adjacent to the distal end 20b of needle 20.

Figure 3:
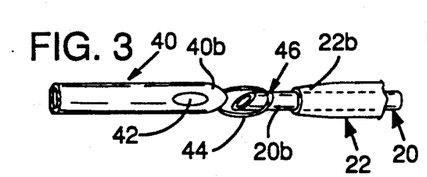
FIGS. 3 and 4 are detailed views of coupling means for releasably coupling and locking together the instrument placement device and the instrument to be drawn into the bladder.
Figure 4:
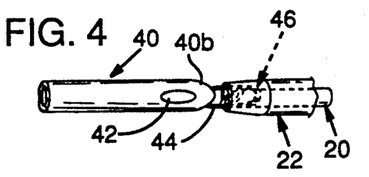

FIG. 3 is a detailed view of the end 40b of catheter 40 and distal end 20b of needle 20. FIG. 3 illustrates the coupling of the loop 44 and indentation 46. As shown in FIG. 3, the distal end 20b of needle 20 extends, by operation of thumb piece 24, beyond the distal end 22b of sheath 22 to expose the indentation 46. Indentation 46 receives the loop 44 of catheter 40 for coupling needle 20 and catheter 40. With reference to FIG. 4, once the loop 44 is positioned and retained within the indentation 46, the distal end 22b of sheath 22 may be advanced by movement of thumb piece 24 (FIG. 2), beyond the distal end 20b of needle 20. In such configuration, the loop 44 is drawn into sheath 22 and lockingly engaged with indentation 46.

Figures 5A, 5B, 5C, 5D, 5E, 5F:
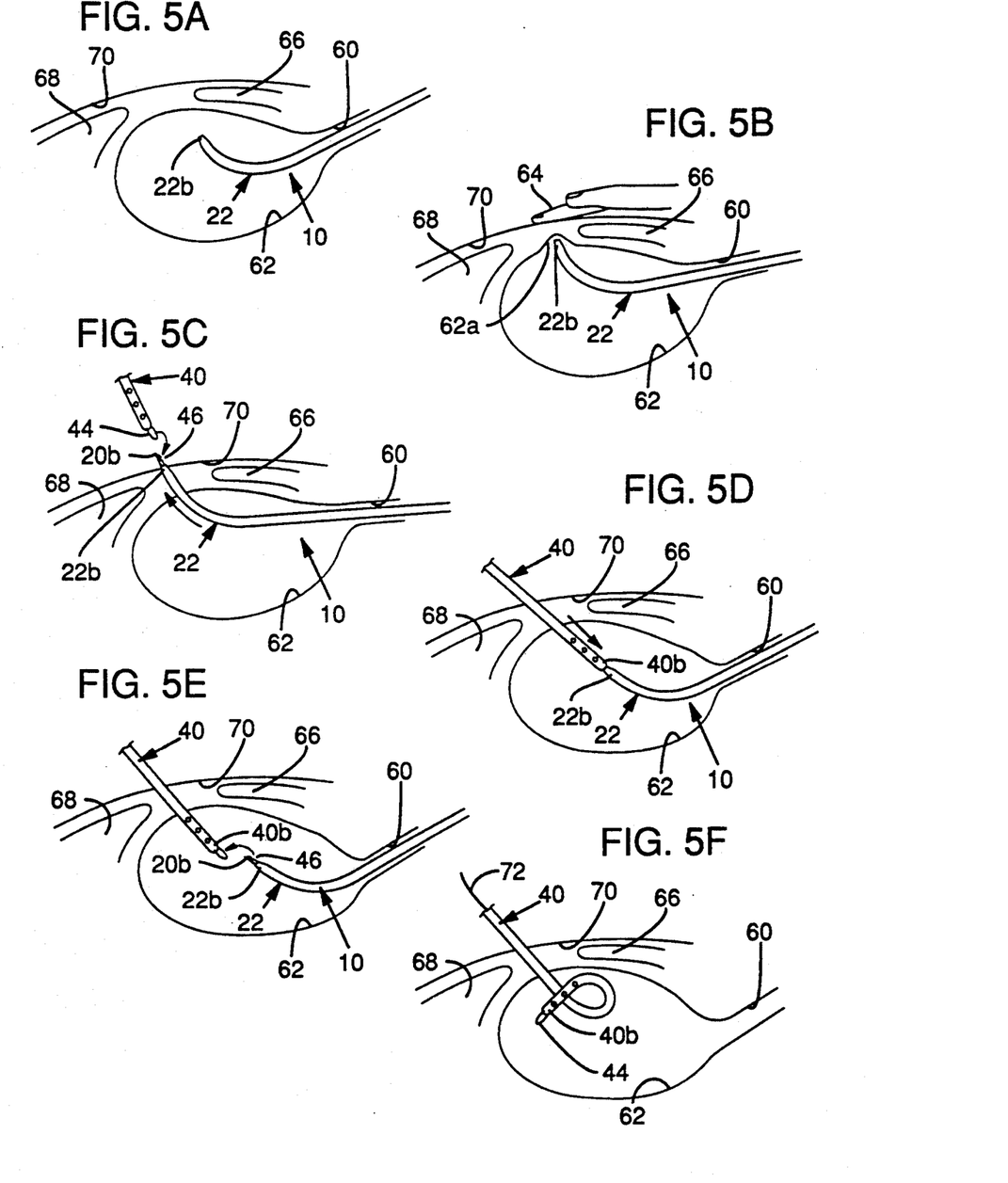
FIGS. 5A–5F illustrate suprapubic instrument placement according to the method of the present invention.

FIGS. 5A-5F illustrate suprapubic instrument placement in accordance with the present invention by use of the device 10 and catheter 40. In FIG. 5A, the device 10 has been inserted through the urethra 60 to position the distal end 22b of sheath 22 within bladder 62. When placing device 10 within bladder 62 the thumb piece 24 is extended to the distal end 14b of slot 14 whereby sheath 22 shrouds the distal end 20b of needle 20. In FIG. 5B, device 10 is lifted against the dome 62a of bladder 62. The practitioner places his or her fingers 64 on the abdomen above the bladder to verify by palpation the positioning of the distal end 22b of device 10. More particularly, the practitioner must position the distal end 22b of device 10 just above the pubic bone 66 and just below the peritoneum 68.

Once the position of device 10 is verified as suitable for suprapubic instrument placement, the thumb piece 24 is drawn back to expose the distal end 20b of needle 20. The point of needle 20, i.e., the distal end 20b, may then be pushed, substantially longitudinally, through the fascia and abdominal wall 70 to the exterior of the abdominal wall 70 as shown in FIG. 5C. In certain cases, a small suprapubic incision may be made to assist advancement of the device 10 through the anterior abdominal wall 70. As shown in FIG. 5C, the distal end 20b of device 10 now protrudes out of the abdominal wall 70 exposing the indentation 46.

The loop 44 of catheter 40 is then coupled to the indentation 46 of device 10. Operation of thumb piece 24 then moves sheath 22 back over the distal end 20b of needle 20 to fully secure the catheter 40 and device 10. Referring now to FIG. 5D, the catheter 40 is then drawn through the abdominal wall 70 and into the bladder 62. Control of catheter location within the bladder is enhanced as traction can be applied at either end of the device assembly until the correct location is determined and the catheter released.

Turning to FIG. 5E, once the end 40b of catheter 40 is suitably positioned within bladder 62, thumb piece 24 is again actuated to expose the distal end 20b of needle 20. Lateral forces applied to the device 10 relative to the catheter 40 release the loop 44 of catheter 40 from the indentation 46. Device 10 may then be removed from the bladder 62 by way of the urethra 60. FIG. 5F shows final positioning of the catheter 40 within bladder 62. More particularly, in the illustrated example the catheter is a J-curve catheter which may be curled into the shape shown in FIG. 5F by withdrawing and securing a string 72 of catheter 40. Once so configured within the bladder 62, catheter 40 is operational.

Thus, the device and method of suprapubic instrument placement according to the present invention avoids many potential hazards of suprapubic instrument placement. For example, before penetrating the bladder wall or abdominal wall, the practitioner may accurately determine the location of the proposed site of catheterization by locating the instrument tip as illustrated in FIG. 5B. This insures that a proper instrument placement site is established.

The nature of the coupling mechanism between the instrument 10 and catheter 40 effects quick and convenient coupling and decoupling, yet provides a very secure coupling while drawing the catheter into the bladder. More particularly, the notch and loop configuration of the coupling means of device 10 and catheter 40 allow convenient coupling and decoupling of these devices, but because the sheath 22 may be positioned over the tip of needle 20, the loop 44 is securely held within the indentation 46. Once the catheter 40 is positioned within the bladder 62, exposing the needle tip and therefore the loop 44 and indentation 46 allows the practitioner to easily decouple the devices.

Additional features of the apparatus of the present invention offer the following benefits. Extravasation is minimized as the catheter size and sheath diameter may be closely matched, by selecting among a variety of sheaths 22, to improve the catheter-bladder seal. The control permitted by the apparatus facilitates its use under local anesthesia. Also, the apparatus may be adapted to place other instruments in the bladder such as cystotomy access tubes, cystourethroscopes, cystolithotriptors and instruments for the treatment of conditions of the bladder prostate urethra, and ureter.

Figures 6, 7:
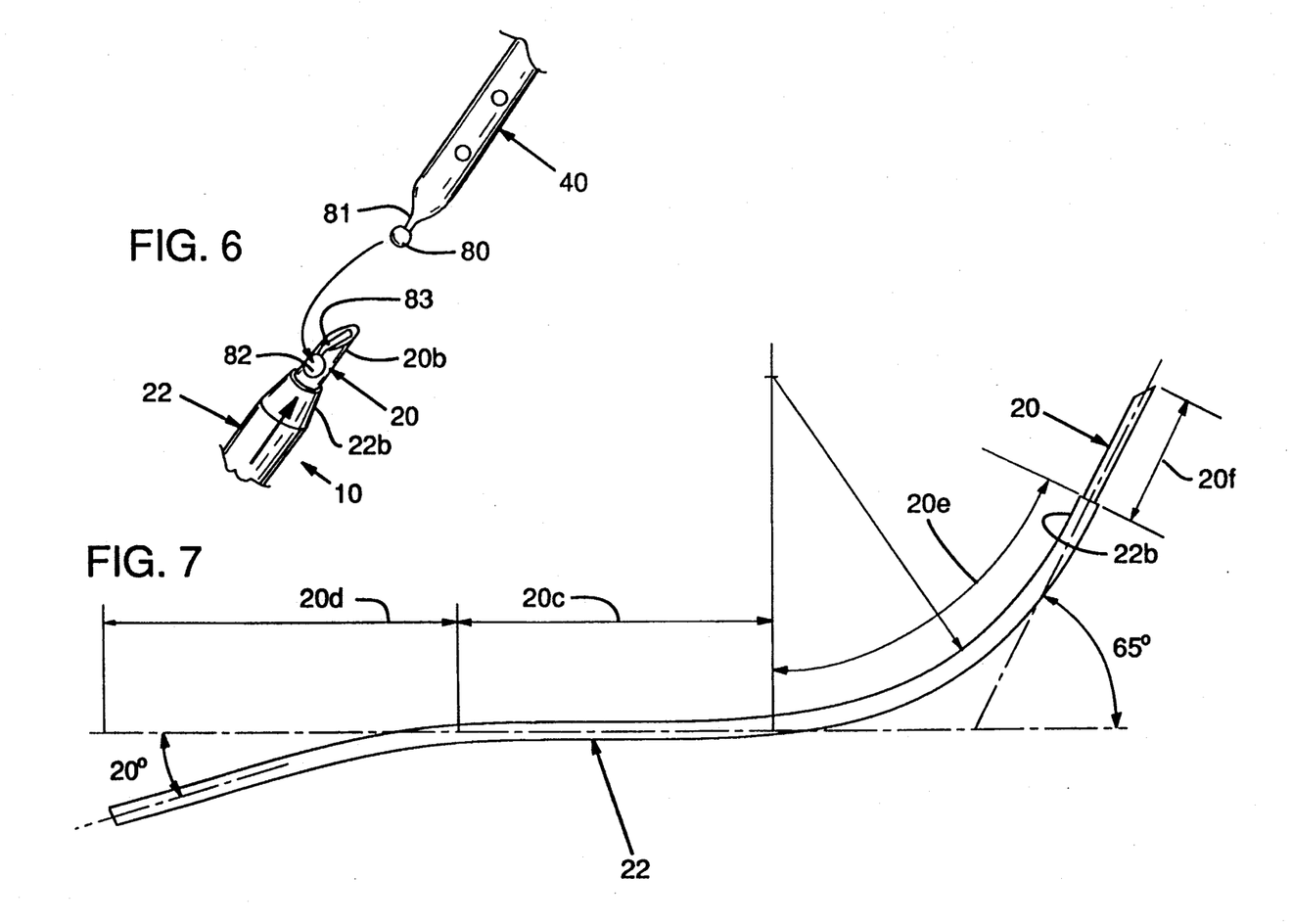
FIG. 6 illustrates an alternative coupling means in accordance with the present invention.
FIG. 7 is a needle and sheath arrangement adapted for placement within the male urethral sound.

The present invention is not limited to the particular coupling means shown in FIG. 3 and FIG. 4 for device 10 and catheter 40. For example, FIG. 6 illustrates an alternative embodiment of the present invention wherein the instrument coupling means comprises a ball 80 attached to the tip of a catheter 40 by a stem 81. A cavity 82 and groove 83 adjacent the distal end 20b of needle 20 receive the ball 80 and stem 81, respectively. To secure the catheter 40 of FIG. 6 and the device 10 of FIG. 6, the ball 80 is positioned within the cavity 82 and the stem within the groove 83. The sheath 22 may then be moved over the distal end 20b of needle 20 to fully secure the ball 80 within the cavity 82. The arrangement of FIG. 6 thereby provides convenient coupling and decoupling while providing a secure locking together of the device 10 and catheter 40 while drawing the catheter 40 into the bladder.

While a J-curve type catheter has been shown for use in connection with the device 10, many forms of catheter and other instruments, e.g. obturators, suitable for suprapubic instrument placement may be used in accordance with the present invention. For example, the types of suprapubic catheters applicable to the present invention include Foleys, Malecots, pigtails and loop-types. The ability to select and align the penetration site and pathway compared to actual penetration minimizes accidental perforation and catheter misplacement.

In the illustrated embodiments of FIGS. 1-5, the sheath-needle assembly comprises a 25 cm length, 13 gauge needle, which is shaped for a female urethra. FIG. 7 illustrates a configuration more suitable for the male urethra. In FIG. 7, needle 20 is shown extended approximately one inch beyond the distal end 22b of sheath 22. As previously described, the needle 20 is desirably a substantially rigid element while the sheath 22 is a flexible member adapted to conform in shape to that of needle 20 while being slidably disposed thereon. In this regard, rigidity in needle 20 may be achieved by use of a stepped-gauge or tapered-gauge needle. A central length portion 20c of needle 20 is approximately 2.5 inches, or 6.35 centimeters. The proximal length portion 20d of needle 20 is approximately three inches, or 7.62 centimeters, and aligned at approximately 20 degrees relative to length portion 20c. A distal length portion 20e of needle 20 is curved along a radius of approximately 2.625 inches, or 6.67 centimeters, extending from the central length portion 20c to the straight distal length portion 20f. The curvatures provided in the needle 20 maintain each length portion of needle 20 within a common plane, with the curvature of portion 20d relative to portion 20c being opposite that of the curvature of portion 20e relative to 20c, i.e., in opposite half-planes as defined by portion 20c. The configuration of needle 20 and sheath 22 as illustrated in FIG. 7 conforms to male anatomy while permitting proper angulation to select suprapubic placement and provide good transfer of longitudinal energy forces.

Suprapubic procedures, as made more available and practical by the present invention, offer many advantages. Suprapubic catheters provide increased patient comfort and minimization of infection in comparison to urethral catheters. Transurethral resection of prostate (TURP) irrigation via a suprapubic tube has been found to maximize visibility and speed resection time. Reduced morbidity and hospital stay can occur when percutaneous bladder procedures are used over open operations. Improving the ease and safety of suprapubic catheter and instrument placement encourages their broader use and allows their benefits to be more fully realized.

Inside-to-outside suprapubic instrument placement in accordance with the present invention further provides full control over catheter placement; accurate suprapubic puncture location and orientation protection of penetrating element (needle); compatibility with a variety of catheter sizes and types; and coordination of puncture diameter with catheter size. Other benefits of suprapubic instrument placement in accordance with the present invention include the capability to fill or drain the bladder, via the needle. It is also possible to inject a local anesthetic through the needle, offering the potential for bedside placement of suprapubic catheters.

Limitations in the application of the apparatus and method of the present invention are few.

For example, in suprapubic instrument placement, urethral obstruction would not permit inside-to-outside access to the bladder. Obesity requires an assistant to pull up on the pannus and then depress down and toward the head. Control of catheter location is enhanced as traction can be applied at either end of the device assembly until the correct location is determined and the catheter is released. The apparatus in accordance with the present invention provides additional benefits such as minimization of extravasation since the catheter diameter and dilating sheath diameter can be closely matched to improve the catheter-bladder wall seal. Catheter loss during placement is substantially minimized as the present invention provides a secure coupling between the placement device and the instrument to be placed. Thus, the apparatus of the present invention offers practitioners, in various surgical fields, a less demanding, and more reliable option for the performance of suprapubic instrument placement.

In addition to the specific embodiments described and illustrated herein, other embodiments are contemplated within the scope of the invention. For example, a rigid sheath may be employed in combination with a flexible needle, or even two rigid components if applicable, wherein the shape of the sheath corresponds to a given anatomy. The coupling mechanism of the present invention is not limited to the inside-to-outside method as it is equally applicable to outside-to-inside methods. Also, the coupling means of the device may be located on the sheath as an alternative to a coupling means on the needle. Transfer tubes, catheters, stents, wire guides, scopes, and other instruments to permit diagnosis and operation may be modified for placement in accordance the present invention. Furthermore, by selecting a different placement site, a variety of instrument devices can be placed, e.g., for cardiovascular, gastroenterology laparoscopy and other situations where indirect means are employed.

Finally, the reliability and control of inside-to-outside suprapubic instrument placement as provided by the present invention will likely generate increased use of suprapubic devices and, therefore, further advance the art of urologic treatment.

We claim:

1. A surgical apparatus for the placement of an instrument within a body cavity which comprises (i) a placement device including an elongate element with an exposable tissue piercing tip, a first coupling means carried by said elongate element and located adjacent to said tip, and means for selectively exposing said tip; and (ii) an elongate portion of said instrument for placement including a second coupling means adapted to be coupled to said first coupling means when said tip has been exposed and operated to pierce a desired tissue site associated with said body cavity and establish a passageway through said tissue; and said first and second coupling means being adapted to be mutually engaged to effect an end to end coupling of said device at said elongate element and said instrument at said elongate portion whereby said instrument is positioned relative to said body cavity by movement of the placement device as coupled in end to end relation with said instrument.

2. An apparatus according to claim 1, in which said first coupling means and said second coupling means are adapted to engage and disengage said device and said instrument in end to end relationship by relative lateral movement therebetween.

3. An apparatus according to claim 2, in which one of said first coupling means and said second coupling means includes locking means for securing said end to end coupling of said device and said instrument against decoupling by relative lateral movement therebetween.

4. An apparatus according to claim 3, in which the elongate element is a needle and said tissue piercing tip is the tip of said needle, said first coupling means is positioned adjacent the needle tip, and said locking means comprises a sheath slidable on said needle, whereby said sheath may be advanced over said needle tip and said first coupling means to selectively shield said tip and to lockingly envelop said second coupling means upon said first coupling means.

5. A placement device for the placement of an instrument within a body cavity, which instrument has a proximal end with instrument coupling means attached thereto, which device comprises:
a needle having a proximal end and a distal end with a tip adapted to pierce body tissue;
a sheath adapted to slidably accommodate said needle, one of said needle and said sheath being substantially rigid and the other of said needle and said sheath being flexible and adapted to conform in shape with the substantially rigid needle or sheath, one of said needle and said sheath having device coupling means adapted to lockingly couple with said instrument coupling means in cooperation with relative sliding movement of said sheath and said needle; and
handle means located at the proximal end of said needle and operatively coupled to said needle and said sheath to enable the needle and sheath to be moved relative to each other to selectively expose the tip of the needle beyond said sheath.

6. A device according to claim 5, in which said device coupling means is an indentation adapted to couple with an instrument coupling means in the form of a loop.

7. A device according to claim 6, in which said indentation is adjacent said needle tip and the engagement of the loop with the indentation is adapted to be lockingly enveloped within the sheath when said sheath is advanced over said needle tip.

8. A device according to claim 5, in which said needle is substantially rigid and said sheath is flexible.

9. A device according to claim 5, in which said instrument is adapted for suprapubic placement and said substantially rigid one of said needle and said sheath is adapted in shape for insertion within a selected urethra.

10. A coupling mechanism for coupling in end to end relation an elongate instrument to an elongate placement device whereby said instrument may be placed within a body cavity by movement of the placement device, which coupling mechanism comprises:
  instrument coupling means attached to a proximal end of said elongate instrument and device coupling means carried by said placement device and located adjacent a distal end of said placement device wherein said instrument coupling means is adapted to operatively engage in end to end relation said device and said instrument or to disengage from said device coupling means by relative lateral movement between said instrument and said device to thereby couple in end to end relation said instrument to said device so that the coupling is sufficiently secure against relative longitudinal movement between said instrument and said device in order to place said instrument; and
  locking means for selectively resisting said lateral movement between said instrument and said device and thereby lock said coupling mechanism.

11. A coupling mechanism according to claim 10, in which said coupling means comprise:
  an indentation on one of said instrument and said device; and
  a loop on the other of said instrument and said device, the loop being adapted to be positioned and retained within said indentation by relative lateral movement between said instrument and said device.

12. A coupling mechanism according to claim 10, in which said locking means comprises a sheath slidably disposed upon one of said instrument and said device and adapted to be slidably moved to envelop said coupling mechanism to resist relative lateral movement between said instrument and said device when said coupling mechanism couples together said instrument and said device.

13. A method for the placement of a suprapubic instrument within the bladder of a patient, which comprises:
  inserting within said patient's urethra a sheathed needle having a distal end with a tissue piercing tip, said needle conforming in shape to the urethra;
  urging said sheathed needle tip against said patient's bladder dome to identify by palpation a penetration site;
  exposing said needle tip from within the sheath and piercing the bladder wall and abdominal wall to deliver tip exterior of the body;
  coupling to the distal end of said needle an instrument to be suprapubicly placed and advancing the sheath over the coupling to avoid disengagement of the coupling;
  drawing said instrument through the abdominal wall and into the bladder by partial retraction of said sheathed needle from the urethral sound;
  positioning said instrument as desired within the bladder;
  decoupling said needle from said instrument; and
  withdrawing said sheathed needle from the urethral sound.

14. A placement device for the placement of an instrument within a body cavity, which instrument has a proximal end with instrument coupling means attached thereto, which device comprises:
  a needle having a proximal end and a distal end with a tip adapted to pierce body tissue;
  a sheath adapted to slidably accommodate said needle, one of said needle and said sheath being substantially rigid and the other of said needle and said sheath being flexible and adapted to conform in shape with the substantially rigid needle or sheath, one of said needle and said sheath having device coupling means adapted to couple with said instrument coupling means; and
  handle means located at the proximal end of said needle and operatively coupled to said needle and said sheath to enable the needle and sheath to be moved relative to each other to selectively expose the tip of the needle beyond said sheath,
  said instrument coupling means comprising a ball and stem attached to said proximal end of the instrument and said device coupling means comprising a cavity and groove adapted to accommodate said ball and stem and the engagement of said two coupling means is adapted to be lockingly enveloped within the sheath when said sheath is advanced over said needle tip.

15. A device according to claim 14, in which said selected urethra is a female urethra and said shape comprises a proximal straight length portion and a distal straight length portion connected by a curved length portion establishing an angular relationship between said proximal and distal portions.

16. A device according to claim 14, in which said selected urethra is a male urethra and said shape comprises a proximal straight length portion, a first curved length portion and a central straight length portion, establishing an angular relationship between said proximal and central portions; a second curved length portion and a distal straight length portion, establishing an angular relationship between said central portion and said distal portion.

17. A coupling mechanism for coupling an elongate instrument to a placement device whereby said instrument may be placed within a body cavity, which coupling mechanism comprises:
  instrument coupling means attached to a proximal end of said elongate instrument and device coupling means adjacent a distal end of said placement device wherein said instrument coupling means is adapted to operatively engage with or disengage from said device coupling means by relative lateral movement between said instrument and said device to thereby couple said instrument to said device so that the coupling is secure against relative longitudinal movement between said instrument and said device, said coupling means comprising a groove and cavity on one of said instrument and said device and a stem and ball on the other of said instrument and said device, said ball being adapted to be accommodated within said cavity by relative lateral movement between said instrument and said device; and locking means for selectively resisting said lateral movement between said instrument and said device and thereby lock said coupling mechanism.

* * * * *